United States Patent
Sarkar et al.

(10) Patent No.: US 11,547,319 B2
(45) Date of Patent: Jan. 10, 2023

(54) MULTILAYERED TABLETS WITH CUSTOMIZED DISSOLVING PATTERNS

(71) Applicant: International Business Machines Corporation, Armonk, NY (US)

(72) Inventors: Biplab Sarkar, Howrah (IN); Saurab Basu, Kolkata (IN); Bijoy Dash, Kolkata (IN); Sarbajit K. Rakshit, Kolkata (IN)

(73) Assignee: International Business Machines Corporation, Armonk, NY (US)

( * ) Notice: Subject to any disclaimer, the term of this patent is extended or adjusted under 35 U.S.C. 154(b) by 612 days.

(21) Appl. No.: 16/674,042

(22) Filed: Nov. 5, 2019

(65) Prior Publication Data

US 2021/0128013 A1    May 6, 2021

(51) Int. Cl.
| | | |
|---|---|---|
| *A61B 5/07* | (2006.01) | |
| *A61B 5/00* | (2006.01) | |
| *B33Y 70/00* | (2020.01) | |
| *B33Y 80/00* | (2015.01) | |
| *B33Y 10/00* | (2015.01) | |

(52) U.S. Cl.
CPC ............ *A61B 5/073* (2013.01); *A61B 5/6861* (2013.01); *B33Y 10/00* (2014.12); *B33Y 70/00* (2014.12); *B33Y 80/00* (2014.12)

(58) Field of Classification Search
CPC ...................................................... A61B 5/073
See application file for complete search history.

(56) References Cited

U.S. PATENT DOCUMENTS

| | | | |
|---|---|---|---|
| 9,633,540 B1 * | 4/2017 | Teshome | A01K 29/005 |
| 9,844,930 B2 | 12/2017 | Hoover et al. | |
| 10,521,561 B1 * | 12/2019 | Euliano | G16H 40/67 |
| 11,357,730 B2 * | 6/2022 | Hafezi | A61P 43/00 |
| 2012/0011699 A1 * | 1/2012 | Hafezi | B30B 11/34 |
| | | | 29/458 |
| 2018/0235881 A1 | 8/2018 | Jiang et al. | |
| 2018/0263913 A1 | 9/2018 | Lefler et al. | |
| 2019/0083073 A1 | 3/2019 | Amoako-Tuffour et al. | |
| 2019/0133958 A1 * | 5/2019 | Hafezi | A61B 5/1473 |
| 2020/0113521 A1 * | 4/2020 | Jones | A61B 5/0031 |
| 2020/0229725 A1 * | 7/2020 | Ruskin | A61B 5/073 |
| 2021/0060317 A1 * | 3/2021 | Pless | A61K 9/0065 |

OTHER PUBLICATIONS

Kong et al., "3D-Printed Gastric Resident Electronics," Advanced Materials Technologies, Communication, 2019, 4, 1800490, pp. 1-11, WILEY-VCH Veriag GmbH & Co.

(Continued)

*Primary Examiner* — Travis R Runnings
(74) *Attorney, Agent, or Firm* — Kelsey M. Skodje

(57) ABSTRACT

A tablet, method of forming the tablet, and article of manufacture that includes the tablet. The tablet can include a layer of a first dissolvable material and a first circuit positioned on the layer of the first dissolvable material. The tablet can also include a layer of a second dissolvable material coating the first circuit, and a second circuit positioned on the layer of the second dissolvable material. The method can include providing the tablet, and determining a dissolving pattern for the tablet.

20 Claims, 2 Drawing Sheets

(56) References Cited

OTHER PUBLICATIONS

Condie, B., "Edible electronics could be providing medical treatments in five years," Cosmos Magazine, Technology Blog, Sep. 22, 2015, 4 pages. https://cosmosmagazine.com/technology/edible-electronics-could-be-providing-medical-treatments-in-five-years.
Tucker, L., "Technology Now Reaching to Food and Drugs with Edible Electronics," maketecheasier, Mar. 6, 2018, 9 pages, https://www.maketecheasier.com/food-drugs-edible-electronics/.
Jain, R., "Edible Sensor That Detects Effects of Food on Body, Digestive Ailments," International Business Times, 1Technology, Oct. 2, 2017, 7 pages. https://www.ibtimes.com/edible-sensor-detects-effects-food-body-digestive-ailments-2600524.
King, T., "Eating Circuits Could Help Obtain More Health Information," ECN Mag Article, Apr. 25, 2018, 5 pages. https://www.ecnmag.com/article/2018/04/eating-circuits-could-help-obtain-more-health-information.
"Edible Electronic Circuits Could be a Medical Revolution in the Waiting," PR Newswire, Apr. 13, 2018, 8 pages. https://www.prnewswire.co.uk/news-releases/edible-electronic-circuits-could-be-a-medical-revolution-in-the-waiting-679629843.html.
Gorey, C., "Would you like some edible graphene on your toast,?" siliconrepublic, Feb. 14, 2018, 18 pages. https://www.siliconrepublic.com/machines/edible-graphene-toast-lasers.
Muhar, L., "The Future of Food-Edible Electronics: "Cute" Laser Designs On Food Will Contain 'RFID Like' Tracking Devices (Video)," Blog, Feb. 19, 2018, 9 pages. https://heiscomingblog.wordpress.com/2018/02/19/the-future-of-food-edible-electronics-cute-laser-designs-on-food-will-contain-rfid-like-tracking-devices-video/.

\* cited by examiner

MULTILAYERED TABLETS WITH CUSTOMIZED DISSOLVING PATTERNS

BACKGROUND

The present disclosure relates to edible circuits and, more specifically, to varying the solubility of layers between circuits in multilayered tablets.

Ingestible circuits are electrical circuits that once ingested transmit signals to an external device (e.g., a wearable electronic device). These circuits can be printed on silicon chips, flexible polymers such as polyimide, or edible materials such as ethyl cellulose. Ingestible circuits can be contained in digestible tablets which, when dissolved, expose the circuit to the surrounding environment (e.g., the gastrointestinal tract). The circuits can then gather data and/or transmit signals from inside the body to an external device (e.g., a wearable electronic device).

SUMMARY

Various embodiments are directed to a tablet that includes layers of a first and a second dissolvable material. The tablet also includes a first circuit (e.g., a graphene circuit) positioned on the layer of the first material and a second circuit positioned on the layer of the second dissolvable material. The layer of the second dissolvable material coats the first circuit. The tablet can also include a layer of a third dissolvable material coating the second circuit and a third circuit positioned on the layer of the third material. The first dissolvable material can be a cellulose, and the second material can be a polysaccharide. The first circuit and the second circuit can transmit signals to a computing device. These signals can provide measurements of physiological parameters.

Additional embodiments are directed to a method that includes providing a tablet (e.g., by three-dimensional (3D) printing) that includes layers of a first and a second dissolvable material. The tablet also includes a first circuit positioned on the layer of the first material and a second circuit positioned on the layer of the second dissolvable material. The layer of the second dissolvable material coats the first circuit. The method also includes determining a dissolving pattern for the tablet. Determining the dissolving pattern can include receiving signals transmitted by the circuits, determining dissolving times for the dissolvable materials based on the signals, and determining the dissolving pattern for the tablet based on the dissolving times. The method can also include storing the dissolving pattern in a user profile. Additionally, the method can include forming a custom tablet that includes at least one circuit and at least one layer of dissolvable material selected from the first and second dissolvable materials. The dissolvable layers of the second tablet can be selected based on the dissolving pattern. A dissolving pattern can be determined for the custom tablet, and the tablet dissolving pattern can be updated to include the dissolving pattern for the custom tablet. The method can also include forming a custom tablet having at least two layers of dissolvable materials independently selected from the first and second dissolvable materials.

Further embodiments are directed to an article of manufacture, which includes a tablet that includes layers of a first and a second dissolvable material. The tablet also includes a first circuit (e.g., a graphene circuit) positioned on the layer of the first material and a second circuit positioned on the layer of the second dissolvable material. The layer of the second dissolvable material coats the first circuit. The first circuit and the second circuit can monitor physiological parameters, and can transmit signals to a wearable computing device.

DETAILED DESCRIPTION

Ingestible circuits are electrical circuits that can be ingested by a human or other animal subject in order to carry out a function within the subject's body. For example, ingestible circuits can be used to measure physiological parameters (e.g., temperature, pH, heart rate, glucose level, oxygen saturation, etc.). These circuits can be printed on silicon chips, flexible polymers such as polyimide, or edible materials such as ethyl cellulose, and can be contained in ingestible tablets. Herein, "ingestible" describes objects that can be taken in for or as if for digestion. However, in some embodiments ingestible objects can be implanted in other ways (e.g., surgical implantation, hypodermic injection, etc.). Ingestible objects can be at least partially edible, though inedible objects (e.g., tablets containing electronic devices such as cameras) can also be ingested. Herein, "edible" describes materials that can be safely dissolved in at least one type of digestive juice (e.g., saliva, stomach acid, bile, etc.). This dissolution can be facilitated by agents such as digestive enzymes and gastrointestinal microbiota.

The amount of time it takes for an edible material to dissolve and/or reach a particular location within a subject's body (e.g., the stomach) varies based on the material and its surroundings. There are differences in surroundings between different individuals, different internal locations, different physiological states (e.g., temperature or acidity), etc. These differences can significantly affect the timing of applications such as environmental sensing and drug delivery. For example, two people can ingest the same type of tablet, but the tablet may not dissolve at the same rate in each person. Similarly, the time it takes for edible materials to dissolve when ingested by one person can vary based on factors such as the time of day (e.g., due circadian temperature variations, food consumption/digestion, etc.).

Customizable ingestible tablets having multiple circuits between layers of edible materials are disclosed herein. The tablet layers are made of materials that dissolve at different rates. A circuit is printed on each layer, and when a layer dissolves, the circuit printed on the next layer is exposed. The exposed circuit then gathers sensory data from its surroundings until the layer on which it is printed has dissolved. This can be repeated a number of times depending on the quantity of layers and circuits in the tablet. Based on the data from the different circuits, a dissolving pattern can be determined. The dissolving pattern indicates how much time it takes each layer to dissolve under the conditions at which the data is collected. This allows tablets to be customized for individuals. For example, a quick-release medication for an individual could be delivered in a tablet of the material with the fastest dissolving time for the individual as determined by a previously ingested multilayered circuit tablet.

Figure 1:
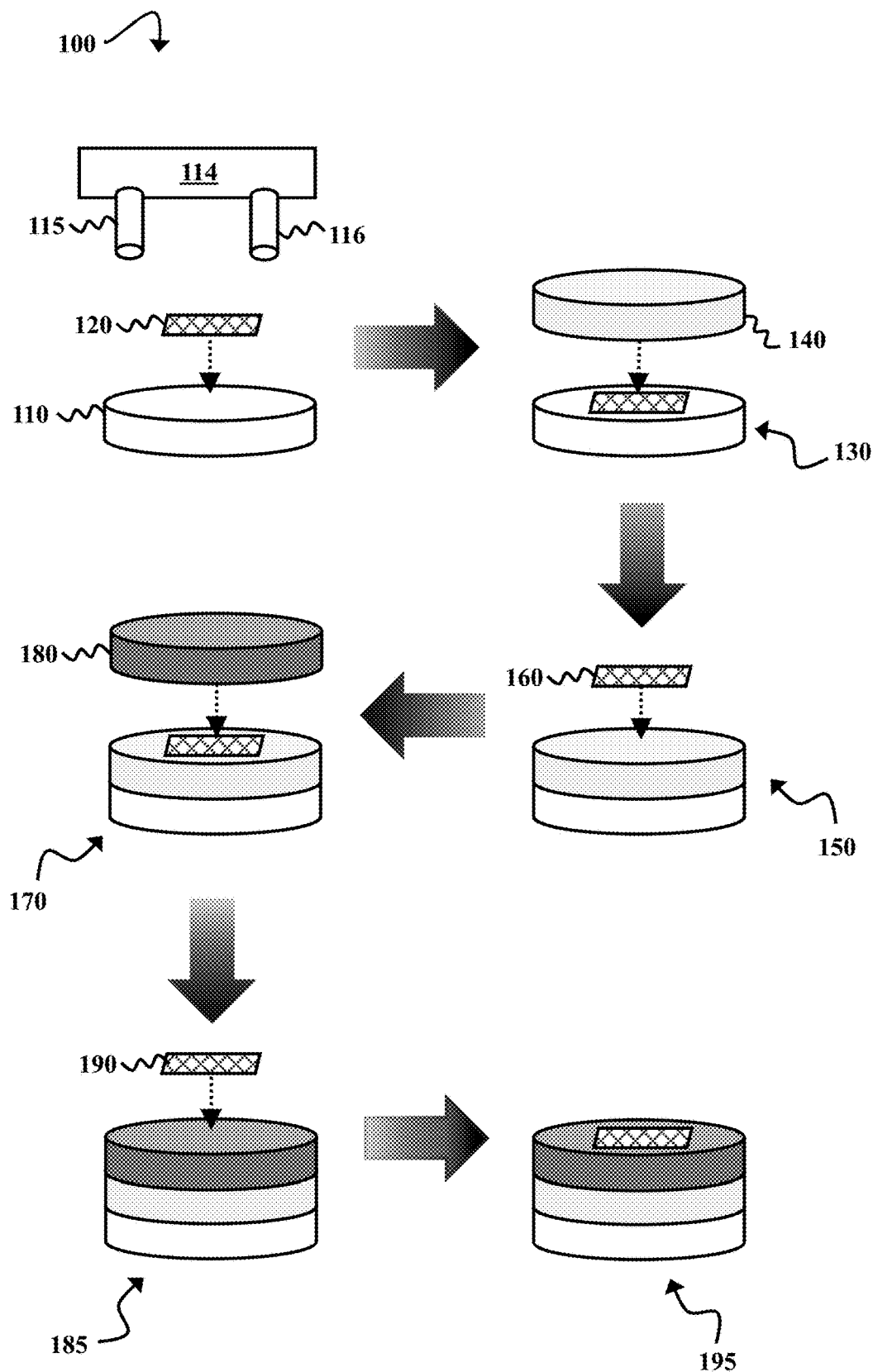
FIG. 1 is a schematic diagram illustrating a process of forming a multilayered tablet, according to some embodiments of the present disclosure.

FIG. 1 is a schematic diagram illustrating a process 100 of forming a multilayered tablet, according to some embodiments of the present disclosure. The tablet is formed using additive manufacturing techniques, such as by 3D printing the circuits and tablet layers. Any appropriate edible tablet materials can be used for the layers. In some embodiments, the layers are made out of different materials, but in other embodiments two or more layers can have the same composition. Examples of tablet materials that can be used can include ethyl cellulose, pullulan, hypromellose, and other polysaccharides or gelatins. Examples of layer materials are discussed in greater detail below. In some embodiments, the circuit material is graphene, though other non-toxic conductive materials can be used as well (e.g., conductive polymers).

A layer 110 of a first material (e.g., ethyl cellulose) is printed by a 3D printer 114. Any 3D printer suitable for printing microelectronics can be used. The printer 114 has at least two nozzles/outputs 115 and 116, one for printing the tablet layers and one for printing the circuit. The printer 114 is used to print each of the subsequent layers as well. A first circuit 120 is then printed on the first material 110, forming a one-layered circuit assembly 130. A layer 140 of a second material is then printed on the one-layered circuit assembly 130 to form a two-layered assembly 150. A second circuit 160 is printed on the second circuit layer 150 to form a two-layered tablet 170. This can be followed by the printing of a third material layer 180 to form a three-layered assembly 185. A third circuit 190 can then be printed on this assembly 185 to form a three-layered tablet 195. In some embodiments, additional circuit layers are added. Further, tablets without an initially exposed circuit can be formed in other embodiments. In these instances, the first circuit does not begin transmitting a signal until the topmost layer has dissolved.

The first, second, third, etc. materials can be selected based on anticipated dissolving times, which are known to persons of ordinary skill. For example, the first layer material (e.g., starches, dextrin, 2-hydroxylpropyl-1-cyclodextrin, etc.) can dissolve faster than the second layer material, which can dissolve faster than the third layer material. For example, second, third, and any subsequent layer materials can be selected from materials such as cellulose acetate phthalate, acrylates, hydroxypropyl methyl cellulose (HPMC), HPMC phthalate, methyl hydroxy cellulose, methyl hydroxyethyl cellulose, ethyl cellulose, polyvinylpyrrolidone (PVP), etc. Additional material parameters can be varied as well (e.g., layer thickness, density, etc.).

Additional components of the tablet 195 are not illustrated in FIG. 1. However, any appropriate additional components can be included. The tablet 195 can also have at least one layer of a dissolvable coating material, which can prevent exposure of the first circuit 120 prior to reaching the desired location of the tablet 195 (e.g., the stomach, intestine, etc.). Coating materials can also be used to mask the taste of the tablet materials, protect the tablet 195 from environmental factors (e.g., corrosion, contamination, etc.) prior to ingestion, etc. Examples of coating materials can include water-soluble starch, dextrin, zein, and polymer films for controlling the release site such as enteric and non-enteric coatings. These polymer films can include polymers such as those used to make the tablet layers 195 (see above). Further, in some embodiments, the circuits can be positioned on layers of a capsule coating (e.g., surrounding an additional electronic component, a pharmaceutical agent in a liquid or powder formulation, etc.), rather than a tablet.

Figure 2:
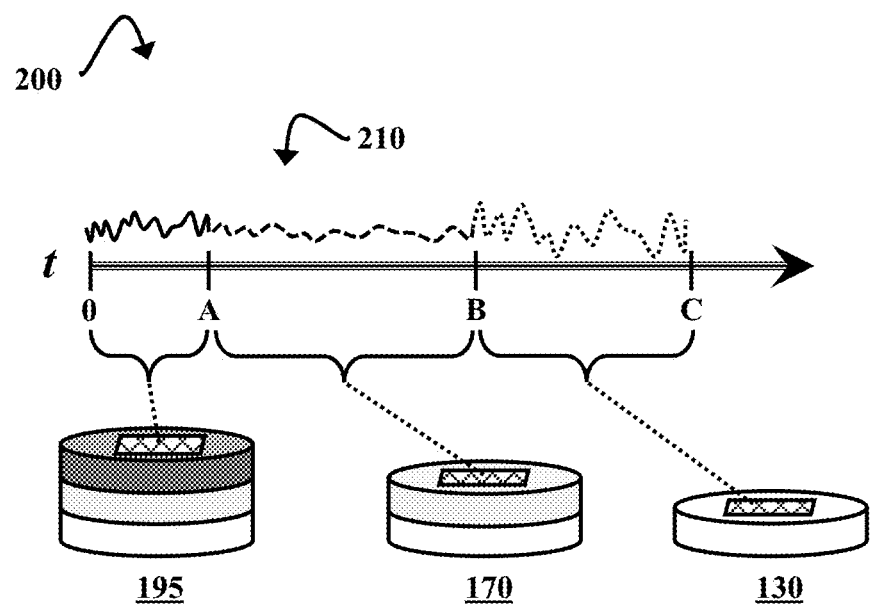
FIG. 2 is a schematic diagram illustrating a process of determining dissolving pattern of a multilayered tablet, according to some embodiments of the present disclosure.

FIG. 2 is a schematic diagram illustrating a process 200 of determining a dissolving pattern 210 of a multilayered tablet, according to some embodiments of the present disclosure. To illustrate process 200, but not to limit embodiments, FIG. 2 is described within the context of process 100 of FIG. 1. Where elements shown in FIG. 2 are identical to elements shown in FIG. 1, the same reference numbers are used in each Figure.

The dissolving pattern 210 includes an arrow representing an amount of time (t) from when the three-layered tablet 195 has been ingested by an individual (t=0) and begun transmitting a first signal (solid line). It should be noted that the dissolving pattern 210 signals shown in FIG. 2 are hypothetical signals drawn for illustrative purposes, and do not represent real data. The signal can be any appropriate signal, depending upon the circuit. For example, the signal can be a measure of temperature, heart rate, respiratory rate, pH, etc. In some embodiments, there is a gap between different signal transmissions. When the top layer of the three-layered tablet 195 has dissolved (t=A), the exposed circuit of the resulting two-layered tablet 170 begins transmitting a second signal (dashed line). The second signal continues until the top layer of the two-layered tablet 170 has dissolved at t=B, whereupon a third signal (dotted line) is transmitted by the exposed circuit of the remaining circuit layer 130. The third signal is transmitted until the final layer 130 is dissolved at t=C.

The transmitted signals are received by a computing device (not shown) such as a wearable device or patch (e.g., a flexible material that adheres to the skin of the individual who has ingested the tablet 195), a mobile device, a desktop computer, or a laptop computer. The computing device processes the signals, and determines each circuit's identity based on its unique signal. The amount of time it takes each layer to dissolve is determined from the duration of each signal, and is recorded in a user profile. The sequence in which the layers dissolve, as well as the duration of each layer's dissolution (t=A, B, and C, respectively), are recorded as the dissolving pattern 210 for the multilayered tablet 195 and the individual who ingested it. The computing device can also analyze the received signals. For example, at least one of the circuits can transmit temperature or pH data.

The dissolving pattern 210 can be saved to a user profile for the individual, along with optional additional information, such as time of day, health information (e.g., medical conditions and/or symptoms), information from other sensors (e.g., a blood pressure monitor), etc. In some embodiments, more than one test tablet can be ingested. Additional test tablets can optionally include different materials, different circuits, different layer sequences, etc. The additional tablets can also be ingested at different times of day, before or after eating, etc., and these conditions can be saved in the user profile along with the dissolving pattern of each tablet. When test tablet containing the same materials as a previous tablet are ingested, the resulting new dissolving pattern data can be used to update the dissolving pattern associated with the previous tablet.

Figure 3:
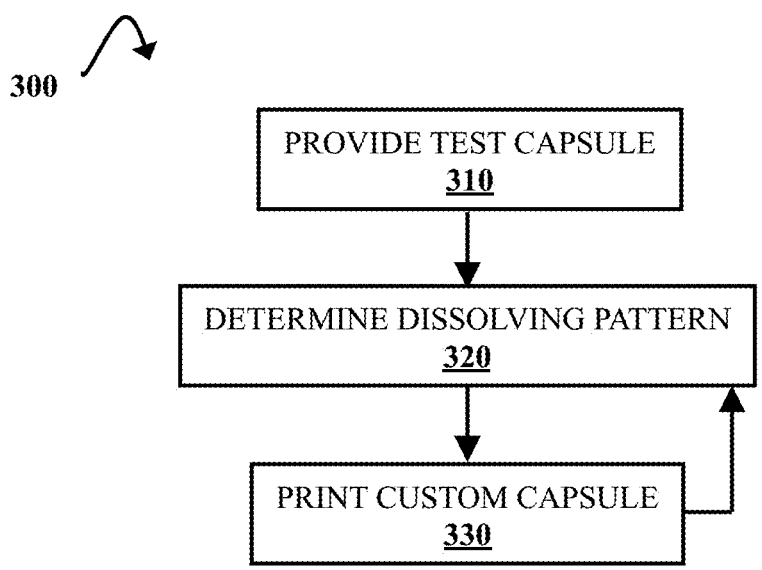
FIG. 3 is a flow diagram illustrating a process of forming a custom multilayered tablet, according to some embodiments of the present disclosure.

FIG. 3 is a flow diagram illustrating a process 300 of forming a customized multilayered tablet, according to some embodiments of the present disclosure. To illustrate process 300, but not to limit embodiments, FIG. 3 is described within the context of processes 100 and 200 of FIGS. 1 and 2. Where elements shown in FIG. 3 are identical to elements shown in FIGS. 1 and 2, the same reference numbers are used in each Figure.

A multilayered test tablet is provided (e.g., the three-layered tablet 195 illustrated in FIGS. 1 and 2). This is illustrated at step 310. The test tablet has at least two circuits (e.g., circuits 120, 160, 190, etc.) printed on layers of dissolvable material. The test tablet is ingested by an individual, and a dissolving pattern is determined for the test tablet. This is illustrated at step 320. The dissolving pattern is determined based on the time and duration of signals transmitted by the circuits. The determination of the dissolving pattern can be carried out using techniques substantially similar to those illustrated in FIG. 2.

A custom tablet is then printed. This is illustrated at step 330. The materials, sequence of layers, circuits, number of layers, etc. used to form the custom tablet are selected based on the dissolving pattern determined at step 320. The dissolving pattern 210 for the test tablet previously ingested by the individual is used to select materials on which to print circuits for a multilayered tablet that will capture signals for these parameters at the desired intervals. For example, a user (e.g., a physician) may want to gather data for various parameters at specific intervals after an individual has consumed food. The user can enter these parameters and/or other information (e.g., selected measurement times, symptoms, a user profile identifier, etc.) into a user interface on a computing device, and the computing device can determine which materials will provide appropriate layers to collect the data. The custom tablet can then automatically be 3D printed. However, in other embodiments, the materials for the layers can be input by the user. Further, the custom tablet can be 3D printed according to user input instructions. The preparation (e.g., 3D printing) of the custom tablet can be carried out using techniques substantially similar to those illustrated at step 310 and in FIG. 1.

Further, in some embodiments the custom tablet can include layers that do not have circuits. For example, a custom tablet can be prepared for a timed release medication or sequence of medications in order to provide precisely timed dosages tailored for the individual. In some instances, the custom tablet can include both circuit layers and non-circuit layers. For example, medication layers can be above circuit layers so that physiological parameters can be monitored after administration of each medication.

Process 300 can end when the custom tablet has been printed at step 330. However, the process 300 can also return to step 320. The signals transmitted by the custom tablet can provide additional dissolving time measurements. That is, the computing device receiving the signals from the circuits can measure the duration of the signals, and record these as a new dissolving pattern. Machine learning techniques (e.g., artificial neural networks) can then be used to update the dissolving pattern 210 or patterns stored in the user profile for the individual by incorporating the additional measurements. This can improve the accuracy of the dissolving pattern 210. Each time an individual ingests a test or custom tablet, the new dissolving pattern data can be added to a user profile for the individual at step 320.

Unless otherwise noted, ranges (e.g., time, concentration, temperature, etc.) indicated herein include both endpoints and all numbers between the endpoints. Unless specified otherwise, the use of "about," "approximately," or a tilde (~) in connection with a range applies to both ends of the range (e.g., "approximately 1 g-5 g" should be interpreted as "approximately 1 g-approximately 5 g"). Unless otherwise indicated, modifying terms such as "about," "approximately," and "~" indicate +/−10% of a recited value, range of values, or endpoints of one or more ranges of values.

The processes discussed herein and their accompanying drawings are not to be construed as limiting. One skilled in the art would recognize that a variety of techniques may be used that vary in conditions, components, methods, etc., which ultimately generate multilayered tablets containing edible circuits. In addition, the conditions can optionally be changed over the course of a process. Further, in some embodiments processes can be added, omitted, or carried out in alternate orders, while still remaining within the scope of the disclosure, as will be understood by a person of ordinary skill in the art. It should also be noted that processes 100-300 can be carried out by a single entity, or by multiple entities. For example, a first entity may print the multilayered tablets, and a second entity may administer the tablets and determine the dissolving patterns.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A tablet, comprising:
    a first layer of a first dissolvable material;
    a first circuit positioned on the layer of the first dissolvable material and having a bottom surface located above a top surface of the first layer;
    a second layer of a second dissolvable material coating the first circuit and having a bottom surface located above a top surface of the first circuit; and
    a second circuit positioned on the layer of the second dissolvable material.

2. The tablet of claim 1, further comprising a layer of a third dissolvable material coating the second circuit.

3. The tablet of claim 2, further comprising a third circuit positioned on the layer of the third dissolvable material.

4. The tablet of claim 1, wherein the first dissolvable material is a cellulose.

5. The tablet of claim 1, wherein the second dissolvable material is a polysaccharide.

6. The tablet of claim 1, wherein the first circuit and the second circuit transmit signals to a computing device.

7. The tablet of claim 6, wherein the signals provide measurements of physiological parameters.

8. The tablet of claim 1, wherein the first circuit is a graphene circuit.

9. A method, comprising:
    providing a tablet, the tablet comprising:
        a first layer of a first dissolvable material;
        a first circuit positioned on the layer of the first dissolvable material and having a bottom surface located above a top surface of the first layer;
        a second layer of a second dissolvable material coating the first circuit and having a bottom surface located above a top surface of the first circuit; and
        a second circuit positioned on the layer of the second dissolvable material; and
    determining a dissolving pattern for the tablet.

10. The method of claim 9, wherein the determining the dissolving pattern comprises:

receiving a first signal, wherein the first signal is transmitted by the first circuit;

determining, based on the first signal, a dissolving time of the first dissolvable material;

receiving a second signal, wherein the second signal is transmitted by the second circuit;

determining, based on the second signal, a dissolving time of the second dissolvable material; and determining, based on the dissolving time of the first dissolvable material and the dissolving time of the second dissolvable material, the dissolving pattern for the tablet.

11. The method of claim 9, further comprising storing the dissolving pattern in a user profile.

12. The method of claim 9, further comprising forming a custom tablet, wherein the custom tablet comprises:

at least one layer of a dissolvable material selected from the group consisting of the first dissolvable material and the second dissolvable material; and at least one circuit positioned on the at least one layer.

13. The method of claim 12, wherein the at least one layer of the dissolvable material is selected based on the dissolving pattern of the tablet.

14. The method of claim 12, further comprising:

determining a dissolving pattern for the custom tablet; and updating the dissolving pattern for the tablet to include the dissolving pattern for the custom tablet.

15. The method of claim 9, further comprising forming a custom tablet, wherein the custom tablet comprises at least two layers of dissolvable materials independently selected from the group consisting of the first dissolvable material and the second dissolvable material.

16. The method of claim 9, wherein the providing the tablet comprises three-dimensional printing.

17. An article of manufacture, comprising:

a tablet, the tablet comprising:

a first layer of a first dissolvable material;

a first circuit positioned on the layer of the first dissolvable material and having a bottom surface located above a top surface of the first layer;

a second layer of a second dissolvable material coating the first circuit and having a bottom surface located above a top surface of the first circuit; and a second circuit positioned on the layer of the second dissolvable material.

18. The article of manufacture of claim 17, wherein the first circuit is a graphene circuit.

19. The article of manufacture of claim 17, wherein the first circuit and the second circuit monitor physiological parameters.

20. The article of manufacture of claim 17, wherein the first circuit and the second circuit transmit signals to a wearable computing device.

* * * * *